United States Patent
Kristen et al.

(10) Patent No.: US 6,846,771 B2
(45) Date of Patent: Jan. 25, 2005

(54) METAL COMPLEXES OF IMINOHYDROXAMIC ACIDS

(75) Inventors: Marc Oliver Kristen, Limburgerhof (DE); Peter Preishuber-Pflügl, Ludwigshafen (DE); Benno Bildstein, Innsbruck (AT); Alexander Krajete, Salzburg (AT)

(73) Assignee: BASF Aktiengesellschaft, Ludwigshafen (DE)

( * ) Notice: Subject to any disclaimer, the term of this patent is extended or adjusted under 35 U.S.C. 154(b) by 43 days.

(21) Appl. No.: 10/359,263

(22) Filed: Feb. 6, 2003

(65) Prior Publication Data

US 2003/0195111 A1 Oct. 16, 2003

(30) Foreign Application Priority Data

Feb. 13, 2002 (DE) .......................... 102 06 116

(51) Int. Cl.[7] .............. B01J 31/38; C08F 4/44
(52) U.S. Cl. ............ 502/155; 502/167; 526/129; 526/161; 526/171; 526/172; 526/346; 526/348; 526/905
(58) Field of Search ................. 502/155, 167; 526/129, 161, 171, 172, 346, 348, 905

(56) References Cited

FOREIGN PATENT DOCUMENTS

| EP | 0 874 005 | 10/1998 |
|---|---|---|
| WO | WO 96/23010 | 8/1996 |
| WO | WO 98/27124 | 6/1998 |

OTHER PUBLICATIONS

H. H. Brintzinger, et al., Angew. Chem. Int. Ed. Engl., vol. 34, pp. 1143–1170, "Stereospecific Olefin Polymerization with Chiral Metallocene Catalysts", 1995.

G. J. P. Britovsek, et al., Angew. Chem. Int. Ed., vol. 38, pp. 428–447, "The Search for New Generation Olefin Polymerization Catalysts: Life Beyond Metallocenes", 1999.

X. Bei, et al., Organometallics, vol. 16, pp. 3282–3302, "Synthesis, Structures, Bonding, and Ethylene Reactivitiy of Group 4 Metal Alkyl Complexes Incorporating 8–Quinolinolato Ligands", 1997.

T. Tsukahara, et al., Organometallics, vol. 16, pp. 3303–3313, "Neutral and Cationic Zirconium Benzyl Complexes Containing Bidentate Pyridine–Alkoxide Ligands. Synthesis and Olefin Polymerization Chemistry of $(pyCR_2O)_2Zr(CH_2Ph)_2$ and $(pyCR_2O)_2Zr(CH_2Ph)\blacklozenge$ Complexes" 1997.

I. Kim, et al., Organometallics, vol. 16, pp. 3314–3323. "Synthesis, Structures, Dynamics, and Olefin Polymerization Behavior of Group 4 Metal $(pyCar_2O)_2M(NR_2)_2$ Complexes Containing Bidentate Pyridine–Alkoxide Ancillary Ligands", 1997.

L. H. Briggs, et al., Aust. J. Chem., vol. 29, pp. 357–366, "Some Hydroxyamidines and Amidoximes", 1976.

*Primary Examiner*—Robert D. Harlan
(74) *Attorney, Agent, or Firm*—Oblon, Spivak, McClelland, Maier & Neustadt, P.C.

(57) ABSTRACT

Complexes of the formulae Ia and Ib

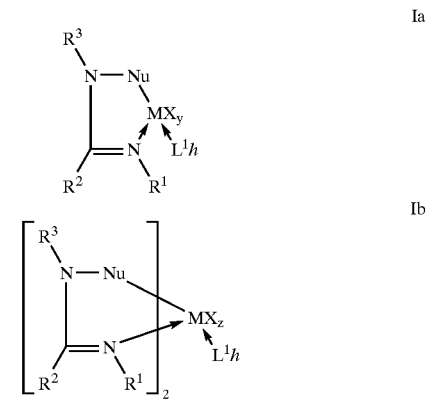

where M=Ti, Zr, Hf, V, Nb, Ta, Cr, Ni, Pd, can be used for the polymerization and copolymerization of olefins, for example in suspension polymerization processes, gas-phase polymerization processes and bulk polymerization processes.

12 Claims, No Drawings

METAL COMPLEXES OF IMINOHYDROXAMIC ACIDS

The present invention relates to complexes of the formulae Ia and Ib,

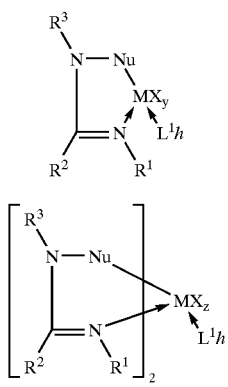

where the variables are defined as follows:
Nu is selected from among O, S, N—$R^4$, P—$R^4$,
M is selected from among Ti, Zr, Hf, V, Nb, Ta, Cr, Ni, Pd;
h is an integer from 0 to 4;
y corresponds to the oxidation state of M minus 1;
z corresponds to the oxidation state of M minus 2, with the proviso that z is greater than zero;
X are identical or different and are selected from among halogen, $C_1$–$C_6$-alkoxy, acetylacetonate, $N(R^5R^6)$, $C_1$–$C_8$-alkyl, $C_3$–$C_{12}$-cycloalkyl, $C_7$–$C_{13}$-aralkyl and $C_6$–$C_{14}$-aryl,
$R^1$, $R^4$ are identical or different and are selected from among hydrogen,
  $C_1$–$C_{18}$-alkyl, substituted or unsubstituted,
  $C_2$–$C_{18}$-alkenyl, substituted or unsubstituted, having from
    1 to 4 isolated or conjugated double bonds;
  $C_3$–$C_{12}$-cycloalkyl, substituted or unsubstituted,
  $C_7$–$C_{13}$-aralkyl,
  $C_6$–$C_{14}$-aryl, unsubstituted or substituted by one or more identical or different substituents selected from among
    $C_1$–$C_{18}$-alkyl, substituted or unsubstituted,
    $C_2$–$C_{18}$-alkenyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy, substituted or unsubstituted,
    $C_6$–$C_{14}$-aryloxy,
    $SiR^5R^6R^7$ and O—$SiR^5R^6R^7$;
  five- to six-membered nitrogen-containing heteroaryl radicals, unsubstituted or substituted by one or more identical or different substituents selected from among
    $C_1$–$C_{18}$-alkyl, substituted or unsubstituted,
    $C_2$–$C_{18}$-alkenyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy,
    $C_6$–$C_{14}$-aryloxy,
    $SiR^5R^6R^7$ and O—$SiR^5R^6R^7$;
$R^2$ $C_6$–$C_{14}$-aryl, unsubstituted or substituted by one or more identical or different substituents, or a five- to six-membered nitrogen-containing heteroaryl radical, unsubstituted or substituted by one or more identical or different substituents, where the substituents are as defined above;
$R^3$ $C_1$–$C_{18}$-alkyl, $C_2$–$C_{18}$-alkenyl, substituted or unsubstituted, having from one to 4 isolated or conjugated double bonds, $C_3$–$C_{12}$-cycloalkyl, substituted or unsubstituted, $C_7$–$C_{13}$-aralkyl, $C_6$–$C_{14}$-aryl, unsubstituted or substituted by or more identical or different substituents, or a five- to six-membered nitrogen-containing heteroaryl radical, unsubstituted or substituted by one or more identical or different substituents, where the substituents are as defined above;
  where adjacent radicals $R^1$ to $R^4$ may be joined to one another to form a 5- to 12-membered ring which may in turn bear substituents selected from among $C_1$–$C_8$-alkyl, substituted or unsubstituted, $C_2$–$C_8$-alkenyl, substituted or unsubstituted, having from one to 4 isolated or conjugated double bonds, $C_3$–$C_{12}$-cycloalkyl, substituted or unsubstituted, $C_7$–$C_{13}$-aralkyl and $C_6$–$C_{14}$-aryl;
$L^1$ is an uncharged organic or inorganic ligand,
$R^5$ and $R^7$ are identical or different and are selected from among hydrogen, $C_1$–$C_8$-alkyl, $C_3$–$C_{12}$-cycloalkyl, $C_7$–$C_{13}$-aralkyl and $C_6$–$C_{14}$-aryl.

Furthermore, the present invention provides a process for the polymerization of olefins using complexes of the formulae Ia and Ib.

Polymers and copolymers of olefins are of great economic importance because the monomers are readily available in large quantities and because the polymers can be varied within a wide range by varying the production process or the processing parameters. In the production process, the catalyst used is of particular significance. Apart from Ziegler-Natta catalysts, various single-site catalysts are of increasing importance, with central atoms which have been examined in detail being Zr, for example in metallocene catalysts (H.-H. Brintzinger et al., *Angew. Chem.* 1995, 107, 1255) and also Ni or Pd (WO 96/23010) and Fe and Co (e.g. WO 98/27124). The complexes of Ni, Pd, Fe and Co are also referred to as complexes of late transition metals.

Metallocene catalysts have disadvantages for industrial use. The most frequently used metallocenes, i.e. zirconocenes and hafnocenes, are sensitive to hydrolysis. In addition, most metallocenes are sensitive to many catalyst poisons such as alcohols, ethers or CO, which makes it necessary for the monomers to be carefully purified.

While Ni or Pd complexes (WO 96/23010) catalyze the formation of the highly branched, commercially less interesting polymers, the use of Fe or Co complexes leads to formation of highly linear polyethylene having a very low comonomer content.

EP-A 0 874 005 discloses further polymerization-active complexes. These are preferably titanium complexes with salicylaldimine ligands. They too bear phenyl substituents or substituted phenyl substituents on the aldimine nitrogen (pages 18–23), or else the aldimine nitrogen is part of a 6-membered ring (pages 31–32). However, they generally produce low molecular weight polyethylenes which are not very suitable as materials. Furthermore, in all the ligands disclosed in EP-A 0 874 005, the oxygen atom is part of a phenolic system, which restricts the choice of readily available starting materials.

As G. J. P. Britovsek et al. demonstrate in *Angew. Chem.* 1999, 111, 448 and *Angew. Chem. Int. Ed. Engl.* 1999, 38, 428, the search for very versatile polymerization-active complexes continues to be important because of the great commercial importance of polyolefins. Particular attention has been paid to complexes of the early transition metals with bidentate ligands, for example complexes of the formula A,

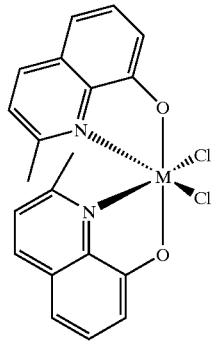

A which have been studied by X. Bei et al. in *Organometallics* 1997, 16, 3282. However, the activities of the complexes in which M=Ti or Zr and in the polymerization of ethylene were too low for the complexes to be of commercial interest. T. Tsukahara et al. in *Organometallics* 1997, 16, 3303 and I. Kim et al. in *Organometallics* 1997, 16, 3314 have examined β-hydroxypyridyl complexes of the formula B

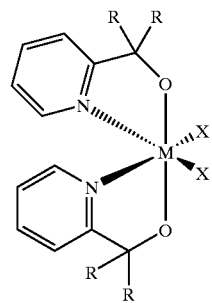

B and their activity in the polymerization of ethylene. If, for example, R is $CH_3$ or $CF_3$ and X is benzyl or neopentyl, the polymerization activity displayed toward ethylene was extremely low or nonexistent when the complex was activated with trispentafluorophenylborane. In contrast, when R was para-tert-butylphenyl and X was benzyl, some activity was observed, but this was too low for commercial purposes.

In Aust. J. Chem. 1976, 29, 357, L. H. Biggs et al. report complexes of the formula C

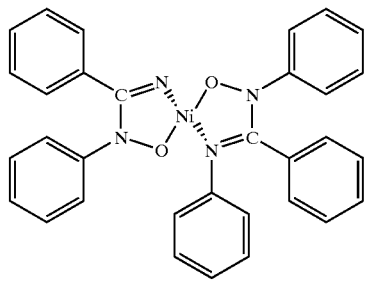

C and examine them for activity against tumors. Complexes of the formula C are polymerization-inactive.

It is an object of the invention to provide novel complexes which are suitable for the polymerization of olefins to give high molecular weight polymers;

to provide a process for preparing the complexes of the present invention;

to provide a process for the polymerization or copolymerization of olefins using the complexes of the present invention;

to provide supported catalysts for the polymerization of olefins and also a process for preparing the supported catalysts of the present invention using the complexes of the present invention;

to polymerize and copolymerize olefins by means of the supported catalysts of the present invention.

We have found that this object is achieved by complexes which have the structures of the formulae Ia and Ib as defined at the outset.

In formula I, the variables are defined as follows:

Nu is selected from among O, S, N—$R^4$ and P—$R^4$, with oxygen and N—$R^4$ being preferred;

M is selected from among Ti, Zr, Hf, V, Nb, Ta, Cr, Ni and Pd in the oxidation states from +2 to +5; preference is given to Ti or Zr in the oxidation state +4 or Ni in the oxidation state +2 and particular preference is given to Zr or Ni;

h is an integer from 0 to 4; in the case of M=Ti or Zr or Hf, h is preferably 0; in the case of M=Ni or Pd, h is preferably not equal to 0 and is particularly preferably 1 or 2;

y corresponds to the oxidation state of M minus 1, z corresponds to the oxidation state of M minus 2, where M can be a metal in the highest oxidation state but does not have to be and z is greater than zero;

X are identical or different and are selected from among halogen, such as fluorine, chlorine, bromine and iodine; preference is given to chlorine or bromine and particular preference is given to chlorine;

$C_1$–$C_6$-alkoxy, such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

acetylacetonate,

N($R^5R^6$), where $R^5$ and $R^6$ are as defined below, particularly preferably N($CH_3$)$_2$, N($CH_3$) ($C_6H_5$) or N($CH_2$)$_4$ $C_1$–$C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

$C_3$–$C_{12}$-cycloalkyl, such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl; and $C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl.

X is preferably halogen. When M is selected from among Ni and Pd,

X is very particularly preferably $C_1$–$C_4$-alkyl or $C_6$–$C_{14}$-aryl.

$R^1$ and $R^4$ are identical or different and are selected from among hydrogen, $C_1$–$C_{18}$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-decyl, n-dodecyl and n-octadecyl; preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_{18}$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl; particular preference is given to fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl;

examples of substituted $C_2$–$C_{18}$-alkenyl groups are: isopropenyl, 1-isoprenyl, α-styryl, β-styryl, 1-cis-1,2-phenylethenyl and 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl und 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, substituted by one or more identical or different substituents selected from among $C_1$–$C_{18}$-alkyl groups such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, isohexyl, sec-hexyl, n-heptyl, isoheptyl n-octyl, n-decyl, n-dodecyl and n-octadecyl; preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl or n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl; particular preference is given to fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl.

examples of substituted $C_2$–$C_{18}$-alkenyl groups are: isopropenyl, 1-isoprenyl, α-styryl, β-styryl, 1-cis-1, 2-phenylethenyl and 1-trans-1,2-phenylethenyl.

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^5R^6R^7$, where $R^5$ to $R^7$ are selected independently from among hydrogen, $C_1$–$C_8$-alkyl groups, the benzyl radical and $C_6$–$C_{14}$-aryl groups; preference is given to the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups $OSiR^5R^6R^7$, where $R^5$ to $R^7$ are selected independently from among hydrogen, $C_1$–$C_8$-alkyl groups, the benzyl radical and $C_6$–$C_{14}$-aryl groups; preference is given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

five- and six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

five- and six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl, substituted by one or more identical or different substituents selected from among $C_1$–$C_{18}$-alkyl groups, such as methyl, ethyl, n-propyl, iso-propyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-decyl, n-dodecyl and n-octadecyl; preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: mono-halogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl; particular preference is given to fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl.

examples of substituted $C_2$–$C_{18}$-alkenyl groups are: isopropenyl, 1-isoprenyl, α-styryl, β-styryl, 1-cis-1,2-phenylethenyl and 1-trans-1,2-phenylethenyl.

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^5R^6R^7$, where $R^5$ to $R^7$ are selected independently from among hydrogen, $C_1$–$C_8$-alkyl groups, the benzyl radical and $C_6$–$C_{14}$-aryl groups; preference is given to the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups $OSiR^5R^6R^7$, where $R^5$ to $R^7$ are selected independently from among hydrogen, $C_1$–$C_8$-alkyl groups, the benzyl radical and $C_6$–$C_{14}$-aryl groups; preference is given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

In a particularly preferred embodiment, $R^1$ or $R^4$ is not hydrogen.

$R^2$ is $C_6$–$C_{14}$-aryl, unsubstituted or substituted by one or more identical or different substituents, or a five- or six-membered nitrogen-containing heteroaryl radical, unsubstituted or substituted by one or more identical or different substituents, where the substituents are as defined above.

$R^3$ and $R^8$ are identical or different and are selected from among $C_1$–$C_{18}$-alkyl, $C_2$–$C_{18}$-alkenyl, substituted or unsubstituted, having from one to 4 isolated or conjugated double bonds, $C_3$–$C_{12}$-cycloalkyl, substituted or unsubstituted, $C_7$–$C_{13}$-aralkyl, $C_6$–$C_{14}$-aryl, unsubstituted or substituted by one or more identical or different substituents, and five- to six-membered nitrogen-containing heteroaryl radicals, unsubstituted or substituted by one or more identical or different substituents, where the substituents are as defined above.

In a particularly preferred embodiment, $R^1$ is selected from among 2,6-diisopropylphenyl, 2,6-dimethylphenyl and ortho-biphenyl.

In a particularly preferred embodiment, $R^2$ is phenyl.

$L^1$ is selected from among uncharged inorganic and organic ligands, for example phosphines of the formula $(R^8)_xPH_{3-x}$ and amines of the formula $(R^8)_xNH_{3-x}$, where x is an integer from 0 to 3. Also suitable are ethers $(R^8)_2O$ such as dialkyl ethers, e.g. diethyl ether, or cyclic ethers, e.g. tetrahydrofuran, $H_2O$, alcohols $(R^8)OH$ such as methanol or ethanol, pyridine, pyridine derivatives of the formula $C_5H_{5-x}(R^8)_xN$, for example 2-picoline, 3-picoline, 4-picoline, 2,3-lutidine, 2,4-lutidine, 2,5-lutidine, 2,6-lutidine or 3,5-lutidine, CO, $C_1$–$C_{12}$-alkyl nitriles or $C_6$–$C_{14}$-aryl nitriles, e.g. acetonitrile, propionitrile, butyronitrile or benzonitrile. It is also possible to use singly or multiply ethylenically unsaturated double bond systems as ligand, e.g. ethenyl, propenyl, cis-2-butenyl, trans-2-butenyl, cyclohexenyl or norbornenyl.

In a particular embodiment, adjacent radicals $R^1$ to $R^4$ in the complexes of the formulae Ia and Ib may be joined to one another to form a 5- to 12-membered ring. For example, $R^3$ and $R^4$ may together be: $-(CH_2)_3-$ (trimethylene), $-(CH_2)_4-$ (tetramethylene), $-(CH_2)_5-$ (pentamethylene), $-(CH_2)_6-$ (hexamethylene), $-CH_2-CH=CH-$, $-CH_2-CH=CH-CH_2-$, $-CH=CH-CH=CH-$, $-O-CH_2-O-$, $-O-CHMe-O-$, $-O-CH-(C_6H_5)-O-$, $-O-CH_2-CH_2-O-$, $-O-CMe_2-O-$, $-NMe-CH_2-CH_2-NMe-$, $-NMe-CH_2-NMe-$ or $-O-SiMe_2-O-$ where $Me=CH_3$. In a further embodiment of the present invention, $R^1$ and $R^6$ are joined to one another to form a 5- to 12-membered ring.

In another preferred embodiment, $L^1$ and X are joined to one another; for example $L^1$ and X can together form an allyl anion or a 2-methylallyl anion.

The complexes required for the process of the present invention can be synthesized readily.

The synthesis of the novel complexes of the formulae Ia and Ib generally starts out from a protonated ligand of the formula II,

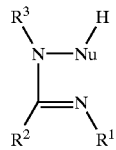

II where the variables are as defined above.

The protonated ligands of the formula II are firstly deprotonated by means of a base and subsequently reacted with metal compounds of the formula $MX_{y+1}$.

As base, it is possible to use the metal alkyls customary in organometallic chemistry, for example methyllithium, ethyllithium, n-butyllithium, sec-butyllithium, tert-butyllithium or hexyllithium, also Grignard compounds such as ethylmagnesium bromide, also lithium amide, sodium amide, potassium amide, potassium hydride or lithium diisopropylamide ("LDA"). Solvents which have been found to be useful are toluene, ortho-xylene, meta-xylene, para-xylene, ethylbenzene or mixtures thereof, also noncyclic or cyclic ethers such as 1,2-dimethoxyethane, tetrahydrofuran or diethyl ether.

This deprotonation is generally complete after a few hours; an appropriate reaction time is from 2 to 10 hours, preferably from 3 to 5 hours. The temperature conditions are generally not critical; carrying out the deprotonation at from $-90°$ C. to $-20°$ C. is preferred.

If a metal compound $MX_{y+1}$ in which X is $C_1$–$C_8$-alkyl, $C_3$–$C_{12}$-cycloalkyl, $C_7$–$C_{13}$-aralkyl or $C_6$–$C_{14}$-aryl is chosen, the use of a base can generally be omitted.

The deprotonated ligand and the metal compound of the formula $MX_{y+1}$ are subsequently reacted with one another.

Here, $MX_{y+1}$ can optionally be stabilized by uncharged ligands. Possible uncharged ligands are the customary ligands of coordination chemistry, for example cyclic and noncyclic ethers, amines, diamines, nitriles, isonitriles or phosphines. Particular preference is given to diethyl ether, tetrahydrofuran, 1,2-dimethoxyethane, tetramethylethylenediamine, acetonitrile or triphenylphosphine.

The conditions for the reaction are not critical per se; it is usual to mix the deprotonated ligand II and $MX_{y+1}$ with one another in a suitable solvent such as benzene, toluene, ethylbenzene, ortho-xylene, meta-xylene or para-xylene, chlorobenzene, cyclohexane, methylene chloride or a mixture thereof. A suitable temperature range is from $-100°$ C. to $+150°$ C., preferably from $-78°$ C. to $+100°$ C. The reaction temperature should not have been below the melting point of the solvent; temperatures above the boiling point of the respective solvent can be achieved in an autoclave. It is important that the reaction is carried out with exclusion of oxygen and moisture.

The molar ratio of ligand to M may be in the range from 5:1 to 1:5. However, since the ligands of the formula II are the reactants which are costlier/more difficult to obtain, preference is given to molar ratios of ligand: M in the range from 1:1 to 1:3, particularly preferably stoichiometric amounts.

If, however, compounds of the formula Ib are to be obtained, molar ratios of ligand: M of from 2:1 to 4:1 are preferred.

The novel complexes of the formulae Ia and Ib can be purified by the methods customary in organometallic chemistry, with crystallization and precipitation being particularly preferred; filtration through filter aids such as Celite® is also useful.

The preparation of the protonated ligands of the formula II is known per se and can be carried out particularly well by reacting an amide of the formula III,

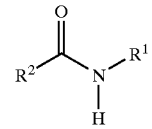

III which bears an acidic α-H atom on the nitrogen, with a halogenating agent such as $SO_2Cl_2$, $PCl_3$ or $POCl_3$ and subsequently reacting the product with a nucleophilic compound of the formula IV,

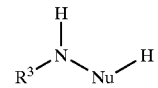

IV where the variables in the compounds III and IV are as defined above, in the presence of a base. By-products formed can be separated off by customary purification methods.

As base, preference is given to using tertiary amines such as triethylamine, diisopropylethylamine or pyridine. Solvents which have been found to be suitable are alcohols or chlorinated hydrocarbons, for example methylene chloride or chloroform, or mixtures thereof; it is also possible to use noncyclic or cyclic ethers such as 1,2-dimethoxyethane, tetrahydrofuran or diethyl ether.

This reaction is generally complete after a period of from a few minutes to a few hours; an appropriate reaction time is from 30 minutes to 10 hours, preferably from 1 to 5 hours. The temperature conditions are generally not critical; preference is given to carrying out the reaction at from −90° C. to +30° C., in exceptional cases up to 50° C.

The reaction is preferably carried out with exclusion of oxygen and moisture.

The molar ratio of III to IV may be in the range from 5:1 to 1:5; preference is given to molar ratios III:IV in the range from 3:1 to 1:3, and particular preference is given to stoichiometric amounts.

Acid amides of the formula III can be obtained by generally known amidation reactions, for example by reaction of carboxylic acids or their esters, carboxylic acid chlorides or carboxylic anhydrides with amines, in the presence or absence of a coupling reagent or a base.

It has been found that the novel complexes of the formulae Ia and Ib are suitable for the polymerization of olefins. They polymerize and copolymerize ethylene and polypropylene particularly well to give high molecular weight polymers. Complexes of the formula Ib are chiral: they can give isotactic polypropylene in the polymerization.

For the novel complexes of the formulae Ia and Ib to be catalytically active, they have to be activated. Suitable activators for complexes in which M is selected from among Ti, Zr, Hf, V, Nb, Ta and Cr are selected aluminum or boron compounds bearing electron-withdrawing radicals (e.g. trispentafluorophenylborane, trispentafluorophenylaluminum, N,N-dimethylanilinium tetrakis (pentafluorophenyl)borate, tri-n-butylammonium tetrakis (pentafluorophenyl)borate, N,N-dimethylanilinium tetrakis (3,5-bisperfluoromethylphenyl) borate, tri-n-butylammonium tetrakis (3,5-bisperfluoromethylphenyl) borate and tritylium tetrakis(pentafluorophenyl)borate. Preference is given to dimethylanilinium tetrakis (pentafluorophenyl)borate, tritylium tetrakis (pentafluorophenyl)borate and trispentafluorophenylborane.

If boron or aluminum compounds are used as activators for the novel compounds of the formulae Ia and Ib, they are generally used in a molar ratio of from 1:10 to 10:1, based on M; preferably from 1:2 to 5:1 and particularly preferably in stoichiometric amounts.

Aluminoxanes form another useful class of activators. The structure of the aluminoxanes is not known precisely. They are products which are obtained by careful partial hydrolysis of aluminum alkyls (cf. DE-A 30 07 725). These products are not in the form of pure single compounds, but are mixtures of open-chain and cyclic structures of the types Va and Vb. These mixtures are presumably in dynamic equilibrium.

In the formulae Va and Vb, the radicals $R^m$ are each, independently of one another,

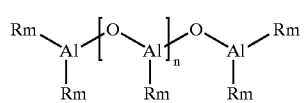

Va

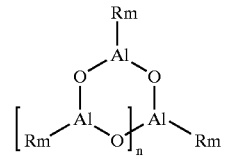

Vb $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl or n-dodecyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably methyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl or cyclododecyl; preference is given to cyclopentyl, cyclohexyl and cycloheptyl;

$C_7$–$C_{20}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, or $C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl, preferably phenyl, 1-naphthyl or 2-naphthyl, particularly preferably phenyl; and n is an integer from 0 to 40, preferably from 1 to 25 and particularly preferably from 2 to 22.

Cage-like structures for aluminoxanes are also discussed in the literature (Y. Koide, S. G. Bott, A. R. Barron *Organometallics* 1996, 15, 2213–26; A. R. Barron *Macromol. Symp.* 1995, 97, 15–25). Regardless of the actual structure of the aluminoxanes, they are suitable as activators for the novel metal complexes of the formulae Ia and Ib.

Mixtures of various aluminoxanes are particularly preferred activators in cases in which the polymerization is carried out in solution in a paraffin, for example n-heptane or isododecane. A particularly prefered mixture is CoMAO which is commercially available from Witco GmbH and has the formula $[(CH_3)_{0.9}(iso\text{-}C_4H_9)_{0.1}AlO]_n$.

To activate the complexes of the formulae Ia and Ib by means of aluminoxanes, it is generally necessary to employ an excess of aluminoxane, based on M. Useful molar ratios M:Al are in the range from 1:10 to 1:10 000, preferably from 1:50 to 1:1000 and particularly preferably from 1:100 to 1:500.

The chosen complex of the formula Ia or Ib and the activator together form a catalyst system.

The activity of the catalyst system according to the present invention can be increased by addition of further aluminum alkyl of the formula $Al(R^m)_3$ or aluminoxanes; aluminum alkyls of the formula $Al(R^m)_3$ or aluminoxanes can also act as molar mass regulators. A further effective molar mass regulator is hydrogen. The molar mass can be regulated particularly well by means of the reaction temperature and the pressure. If the use of a boron compound as described above is desired, the addition of an aluminum alkyl of the formula $Al(R^m)_3$ is particularly preferred.

When M is Ni or Pd, preference is given to using olefin complexes of rhodium or nickel as activator.

Preferred nickel(olefin)$_y$ complexes with y=1, 2, 3 or 4 which are commercially available, e.g. from Aldrich, are Ni(C$_2$H$_4$)$_3$, Ni(1,5-cyclooctadiene)$_2$ "Ni(COD)$_2$", Ni(1,6-cyclodecadiene)$_2$ and Ni(1,5,9-all-trans-cyclododecatriene)$_2$. Particular preference is given to Ni(COD)$_2$.

Particularly useful olefin complexes are mixed ethylene/1,3-dicarbonyl complexes of rhodium, for example (ethylene)rhodium acetylacetonate Rh(acac) (CH$_2$=CH$_2$)$_2$, (ethylene)rhodium benzoylacetonate Rh(C$_6$H$_5$—CO—CH—CO—CH$_3$) (CH$_2$=CH$_2$)$_2$ or Rh(C$_6$H$_5$—CO—CH—CO—C$_6$H$_5$) (CH$_2$=CH$_2$)$_2$. The most useful complex is Rh(acac) (CH$_2$=CH$_2$)$_2$. This compound can be synthesized by the method described by R. Cramer in *Inorg. Synth.* 1974, 15, 14.

Some complexes of the formula Ia can be activated by means of ethylene. The ease of the activation reaction depends critically on the nature of the ligand L$^1$.

Pressure and temperature conditions during the polymerization can be chosen within wide limits. A pressure in the range from 0.5 bar to 4000 bar has been found to be useful; preference is given to from 10 to 75 bar or high-pressure conditions of from 500 to 2500 bar.

A suitable temperature range has been found to be from 0 to 120° C., preferably from 40 to 100° C. and particularly preferably from 50 to 85° C.

As monomers, mention may be made of the following olefines: ethylene, propylene, 1-butene, 1-pentene, 1-hexene, 1-octene, 1-decene and 1-undecene, with propylene and ethylene being preferred and ethylene being particularly preferred. Styrene can also be used as monomer.

Suitable comonomers are α-olefins, for example from 0.1 to 20 mol % of 1-butene, 1-pentene, 1-hexene, 4-methyl-1-pentene, 1-octene, 1-decene or 1-undecene. However, isobutene and styrene are also suitable comonomers, also internal olefins such as cyclopentene, cyclohexene, norbornene and norbornadiene.

As solvents, toluene, ortho-xylene, meta-xylene, para-xylene, ethylbenzene and mixtures thereof have been found to be useful. Supercritical ethylene can also be employed under high-pressure conditions.

The catalyst systems of the present invention polymerize olefins to give polyolefins having a very high molecular weight.

The catalyst systems of the present invention can be regulated by means of hydrogen in the polymerization, i.e. the molecular weight of the polymers obtainable by means of the catalyst system of the present invention can be reduced by addition of hydrogen. If sufficient hydrogen is added, polyolefin waxes are obtained. The preferred concentration of hydrogen also depends on the type of polymerization plant used.

For the catalyst systems of the present invention to be able to be used in modern polymerization processes such as suspension processes, bulk polymerization processes or gas-phase processes, it is necessary for them to be immobilized on a solid support. Otherwise, morphology problems with the polymer (lumps, deposits on walls, blockages in lines or heat exchangers) can occur and force shutdown of the plant. Such an immobilized catalyst system is referred to as catalyst.

The catalyst systems of the present invention can be deposited on solid support materials. Possible support materials are, for example, porous oxides of metals of groups 2 to 14 or mixtures thereof, also sheet silicates and zeolites. Preferred examples of metal oxides of groups 2 to 14 are SiO$_2$, B$_2$O$_3$, Al$_2$O$_3$, MgO, CaO and ZnO. Preferred sheet silicates are montmorillonites or bentonites; as zeolite, preference is given to using MCM-41.

Particularly preferred support materials are spherical silica gels and aluminosilicate gels of the formula SiO$_2$.a Al$_2$O$_3$, where a is generally in the range from 0 to 2, preferably from 0 to 0.5. Such silica gels are commercially available, e.g. silica gel SG 332, Sylopol® 948 or 952 or S 2101 from W. R. Grace or ES 70X from Crosfield.

Suitable particle sizes of the support material are mean particle diameters in the range from 1 to 300 μm, preferably from 20 to 80 μm, as determined by known methods such as sieving. The pore volume of the support is from 1.0 to 3.0 ml/g, preferably from 1.6 to 2.2 ml/g and particularly preferably from 1.7 to 1.9 ml/g. The BET surface area is from 200 to 750 m$^2$/g, preferably from 250 to 400 m$^2$/g.

To remove impurities, in particular moisture, adhering to the support material, the support materials can be baked before application of the active catalyst complex. Suitable temperatures for this are in the range from 45 to 1000° C. Temperatures of from 100 to 750° C. are particularly suitable for silica gels and other metal oxides. This baking can be carried out over a period of from 0.5 to 24 hours, with times of from 1 to 12 hours being preferred. The pressure conditions are dependent on the process chosen; baking can be carried out in a fixed bed, a stirred vessel or else in a fluidized bed. Baking can be carried out at atmospheric pressure, but reduced pressures of from 0.1 to 500 mbar are advantageous. A range from 1 to 100 mbar is particularly advantageous and a range from 2 to 20 mbar is very particularly advantageous. On the other hand, fluidized-bed processes are advantageously carried out at a slightly superatmospheric pressure in the range from 1.01 bar to 5 bar, preferably from 1.1 to 1.5 bar.

Chemical pretreatment of the support material with an alkyl compound such as an aluminum alkyl, a lithium alkyl or an aluminoxane is likewise possible.

In a suspension polymerization, use is made of suspension media in which the desired polymer is insoluble or only slightly soluble, because otherwise deposits of product are obtained in plant components in which the product is separated from the suspension medium and this makes repeated shutdowns and cleaning operations necessary. Suitable suspension media are saturated hydrocarbons such as propane, n-butane, isobutane, n-pentane, isopentane, n-hexane, isohexane and cyclohexane, with isobutane being preferred.

Pressure and temperature conditions during the polymerization can be chosen within wide limits. A pressure in the range from 0.5 bar to 150 bar has been found to be useful; preference is given to from 10 to 75 bar. A suitable temperature range has been found to be from 0 to 120° C., preferably from 40 to 100° C.

As monomers, mention may be made of the following olefins: ethylene, propylene, 1-butene, 1-pentene, 1-hexene, 1-octene, 1-decene and 1-undecene. Styrene can also be used as monomer.

Suitable comonomers are α-olefins, for example from 0.1 to 20 mol % of 1-butene, 1-pentene, 1-hexene, 4-methyl-1-pentene, 1-octene, 1-decene or 1-undecene. However, isobutene and styrene are also suitable comonomers, also internal olefins such as cyclopentene, cyclohexene, norbornene and norbornadiene.

The catalysts of the present invention have, overall, an advantageous use profile in process engineering terms.

Furthermore, the catalysts of the present invention have been found to be able to be regulated by means of hydrogen, i.e. the molecular weight of the polymers obtainable by means of the catalysts of the present invention can be reduced by addition of hydrogen. Waxes are obtained when sufficient hydrogen is added, with the hydrogen concentration required also depending on the type of polymerization plant used. Addition of hydrogen generally increases the activity of the catalysts of the present invention.

The catalysts of the present invention can also be used together with one or more other polymerization catalysts known per se. Thus, for example, they can be used together with Ziegler-Natta catalysts, supported metallocene catalysts containing transition metals of groups 4 to 6 of the Periodic Table of the Elements, catalysts based on late transition metals (WO 96/23010), Fe or Co complexes with pyridyldiimine ligands, as are disclosed in WO 98/27124, or chromium oxide catalysts of the Phillips type.

If a number of catalysts are used, it is possible to mix various catalysts with one another and to introduce them together into the polymerization or to use cosupported complexes on a common support or else to meter various catalysts separately into the polymerization vessel at the same point or at different points.

Furthermore, it has been found that the novel complexes of the formulae Ia and Ib, in particular those in which M=Ni, are particularly useful for the polymerization or copolymerization of 1-olefins, preferably ethylene, in emulsion polymerization processes.

Apart from other 1-olefins as comonomers, for example propene, 1-butene, 1-hexene, 1-octene or 1-decene, or vinylaromatic compounds such as styrene, it is also possible for polar comonomers to be incorporated by means of the catalyst system of the present invention, with from 0.1 to 50 mol % of comonomers being able to be used. Preference is given to acrylates such as acrylic acid, methyl acrylate, ethyl acrylate, 2-ethylhexyl acrylate, n-butyl acrylate or tert-butyl acrylate;

methacrylic acid, methyl methacrylate, ethyl methacrylate, n-butyl methacrylate or tert-butyl methacrylate;

vinylaromatic compounds such as styrene;

vinyl carboxylates, particularly preferably vinyl acetate, unsaturated dicarboxylic acids, particularly preferably maleic acid, unsaturated dicarboxylic acid derivatives, particularly preferably maleic anhydride and alkylimides of maleic acid, e.g. the methylimide of maleic acid.

It is also possible to prepare terpolymers comprising at least 2 of the abovementioned monomers together with ethylene.

The emulsion polymerization of the 1-olefins using the metal complexes of the formula I as provided by the present invention can be carried out in a manner known per se.

The order of addition of the reagents in the polymerization is not critical. Thus, the solvent can firstly be pressurized with gaseous monomer or liquid monomer can be metered in, followed by addition of the catalyst system. However, it is also possible for the solution of the catalyst system firstly to be diluted with further solvent and the monomer to be added subsequently.

The actual polymerization is usually carried out at a minimum pressure of 1 bar; below this pressure, the polymerization rate is too low. Preference is given to 2 bar and particular preference is given to a minimum pressure of 10 bar.

A practical maximum pressure is 4000 bar; at higher pressures, the demands made of the material of which the polymerization reactor is constructed are very high and the process becomes uneconomical. Preference is given to 100 bar and particular preference is given to 50 bar.

The polymerization temperature can be varied within a wide range. A practical minimum temperature is 10° C., since the polymerization rate decreases at low temperatures. Preference is given to a minimum temperature of 40° C., particularly preferably 65° C. The maximum practical temperature is 350° C. and preference is given to a maximum temperature of 150° C., particularly preferably 100° C.

Before the polymerization, the complex of the formula Ia or Ib is dissolved in an organic solvent or in water. The solution is stirred or shaken for a number of minutes to ensure that it is clear. The stirring time can, depending on the solubility of the complex concerned, be from 1 to 100 minutes.

At the same time, any activator necessary is dissolved in a second portion of the same solvent or else in acetone.

Suitable organic solvents are aromatic solvents such as benzene, toluene, ethylbenzene, ortho-xylene, meta-xylene and para-xylene and mixtures thereof. Also suitable are cyclic ethers such as tetrahydrofuran and dioxane or non-cyclic ethers such as diethyl ether, di-n-butyl ether, diisopropyl ether or 1,2-dimethoxyethane. It is also possible to use ketones such as acetone, methyl ethyl ketone or diisobutyl ketone, likewise amides such as dimethylformamide or dimethylacetamide. Mixtures of these solvents with one another and also mixtures of these solvents with water or alcohols such as methanol or ethanol are also possible.

Preference is given to acetone and water and mixtures of acetone and water, with any mixing ratio being possible. The amount of solvent is likewise not critical, but it has to be ensured that the complex and the activator can dissolve completely, otherwise a reduced activity has to be expected. The dissolution can, if appropriate, be accelerated by ultrasonic treatment.

If an emulsifier is to be added, it can be dissolved in a third portion of the solvent or else together with the complex. The amount of any such emulsifier is selected so that the mass ratio of monomer to emulsifier is greater than 1, preferably greater than 10 and particularly preferably greater than 20. The less emulsifier which has to be used, the better. The activity of the polymerization is significantly increased if an emulsifier is added. This emulsifier can be nonionic or ionic in nature.

Nonionic emulsifiers which can be used are, for example, ethoxylated monoalkylphenols, dialkylphenols and trialkylphenols (EO content: 3–50, alkyl radical: $C_4$–$C_{12}$) and ethoxylated fatty alcohols (EO content: 3–80; alkyl radical: $C_8$–$C_{36}$). Examples are the Lutensol® grades from BASF AG or the Triton® grades from Union Carbide.

Customary anionic emulsifiers are, for example, alkali metal and ammonium salts of alkyl sulfates (alkyl radical: $C_8$ to $C_{12}$), of sulfuric monoesters of ethoxylated alkanols (EO content: 4–30, alkyl radical: $C_{12}$–$C_{18}$) and ethoxylated alkylphenols (EO content: 3–50, alkyl radical: $C_4$–$C_{12}$), of alkylsulfonic acids (alkyl radical: $C_{12}$–$C_{18}$) and of alkylarylsulfonic acids (alkyl radical: $C_9$–$C_{18}$).

Suitable cationic emulsifiers are, in general, primary, secondary, tertiary or quaternary ammonium salts containing a $C_6$–$C_{18}$-alkyl, -aralkyl or heterocyclic radical, alkanolammonium salts, pyridinium salts, imidazolinium salts, oxazolinium salts, morpholinium salts, thiazolinium salts and salts of amine oxides, quinolinium salts, isoquinolinium salts, tropylium salts, sulfonium salts and phosphonium salts. Examples which may be mentioned are dodecylammonium acetate and the corresponding hydrochloride, the chlorides or acetates of the various 2-(N,N,N-trimethylammonio)ethyl paraffinic acid esters, N-cetylpyridinium chloride, N-laurylpyridinium sulfate and N-cetyl-N,N,N-trimethylammonium bromide, N-dodecyl-N,N,N-trimethylammonium bromide, N,N-distearyl-N,N-dimethylammonium chloride and also the gemini surfactant N,N'-(lauryldimethyl)ethylenediamine dibromide. Numerous further examples may be found in H. Stache, *Tensid-Taschenbuch*, Carl-Hanser-Verlag, Munich, Vienna, 1981, and in McCutcheon's, *Emulsifiers & Detergents*, MC Publishing Company, Glen Rock, 1989.

The components, i.e. complex in solution, optionally the solution of the emulsifier and optionally the solution of the activator, are subsequently introduced into the polymerization reactor.

Polymerization reactors which can be used are stirred tanks and autoclaves and also tube reactors, with the tube reactors being able to be configured as loop reactors.

The monomer or monomers to be polymerized are mixed with the polymerization medium. As polymerization medium, it is possible to use water or mixtures of water with the abovementioned solvents. It should be ensured that the proportion of water is at least 50% by volume, based on the total mixture, preferably at least 90% by volume and particularly preferably at least 95% by volume.

The solutions of the complex, of any activator used and of any emulsifier used are combined with the mixture of monomer and aqueous polymerization medium. The order of addition of the various components is not critical per se. However, it is necessary for the components to be combined sufficiently quickly for no crystallization of any sparingly soluble complexes formed as intermediates to occur.

The process of the present invention gives polyolefins and olefin copolymers in high yields, i.e. the activity of the complexes of the present invention under the conditions of emulsion polymerization is very high.

In principle, both continuous and batchwise processes are suitable as polymerization processes. Preference is given to semicontinuous processes (semibatch processes) in which all components are mixed and further monomer or monomer mixture is metered in during the course of the polymerization.

The process of the present invention initially gives aqueous polymer dispersions.

The mean particle diameter of the polymer particles in the dispersions obtained according to the present invention is from 10 to 1000 nm, preferably from 50 to 500 nm and particularly preferably from 70 to 350 nm. The distribution of the particle diameters can be very uniform, but does not have to be. For some applications, in particular those in which the solids content is high (>55%), broad or bimodal distributions may even be preferred.

The polymers obtained by the process of the present invention have technically interesting properties. In the case of polyethylene, they have a high degree of crystallinity, which can be seen, for example, from the number of branches. The number of branches found is less than 100, preferably less than 50, per 1000 carbon atoms of the polymer as determined by $^1$H-NMR and $^{13}$C-NMR spectroscopy.

The enthalpies of fusion of the polyethylenes obtainable by the process of the present invention are greater than 100 J/g, preferably greater then 140 J/g and particularly preferably greater than 180 J/g, measured by DSC.

The molecular weight distributions of the polyethylenes obtainable by the process of the present invention are narrow, i.e. the Q values are in the range from 1.1 to 3.5, particularly preferably from 1.5 to 3.1.

Advantages of the dispersions obtained according to the present invention are not only the low price due to the cheap monomers and process but also a better weathering resistance than dispersions of polybutadiene or butadiene copolymers. Compared to dispersions of polymers comprising acrylates or methacrylates as main monomer, the low tendency to undergo hydrolysis is advantageous. Another advantage is that most olefins are volatile and residual unpolymerized monomers can easily be removed. A final advantage is that the polymerization does not require addition of molar mass regulators such as tert-dodecyl mercaptan which are not only difficult to separate off but also have an unpleasant odor.

The polymer particles can be obtained as such by removing the water and, if present, the organic solvent or solvents from the aqueous dispersions obtained initially. Numerous customary methods are suitable for removing the water and any organic solvent or solvents, for example filtration, spray drying or evaporation. The polymers obtained in this way have a good morphology and a high bulk density.

The particle size can be determined by light scattering methods. An overview may be found in D. Distler "WäBrige Polymerdispersionen", Wiley-VCH, 1st edition, 1999, chapter 4.

The dispersions obtained according to the present invention can be used advantageously in numerous applications, for example paper applications such as paper coating or surface sizing, also paints and varnishes, building chemicals, adhesives raw materials, molded foams, textile and leather treatments, coatings on the reverse side of carpets, mattresses or pharmaceutical applications.

The following examples illustrate the invention.

General preliminary remarks:

All work was, unless indicated otherwise, carried out with exclusion of air and moisture using standard Schlenk techniques. Apparatus and chemicals were prepared appropriately. The polymer viscosity was determined in accordance with ISO 1628-3.

1. Preperation of the Protonated Ligands II 1.1. Preparation of the Protonated Ligand II.1

The synthesis of the protonated ligands is illustrated, by way of example, by the description of the synthesis of II.1.

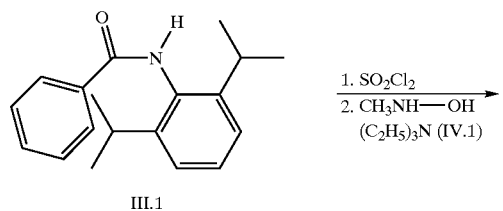

III.1

-continued

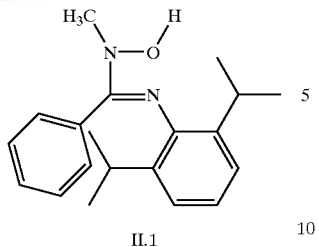

II.1 a) 1.9 g of N-(2,6-diisopropylphenyl)benzamide (6.7 mmol) were placed in a dry Schlenk tube which had been flushed with argon. After addition of 10 ml of thionyl chloride, the reaction solution was refluxed for 60 minutes. Excess $SOCl_2$ was taken off in a high vacuum and the yellow oil which remained was dissolved in 20 ml of methylene chloride (absolute).

b) N-Methylhydroxylamine hydrochloride IV.1 (0.56 g, 6.7 mmol) was placed in a Schlenk tube which had been baked out and flushed with argon and was dissolved in absolute ethanol (50 ml). After addition of 10 ml of triethylamine (72 mmol), the suspension formed was cooled to −40° C.

The imide chloride III.1 which had been prepared and dissolved in methylene chloride under a) was slowly added from a dropping funnel to the solution b) at −40° C. over a period of 30 minutes. After warming to room temperature, the reaction mixture (yellow suspension) was stirred for 1 hour. Subsequent thin layer chromatography (diethyl ether) of the reaction mixture indicated complete conversion.

The reaction mixture was poured into water (about 100 ml), and the product was extracted 3× with 50 ml each time of diethyl ether. The organic phase was dried over $Na_2SO_4$, and the desiccant was filtered off. After the solvent had been distilled off on a rotary evaporator, the semicrystalline solid formed was dissolved in small amounts of methylene chloride and filtered through silica gel. The nonpolar component, which was very readily soluble in ether, was completely separated off in this way, and the polar component was enriched on the silica gel. The polar target product was eluted by means of about 200 ml of ethanol in a water pump vacuum.

The solvent was subsequently distilled off on a rotary evaporator, then in a high vacuum. The resulting whitish beige solid gave, as a solution in ethanol, a deep violet color with $FeCl_3$: an indication of the presence of a hydroxamic acid derivative. II.1 could be obtained in high purity by solid phase extraction (stationary phase: silica gel 60 from Merck KGaA; eluant 1: diethyl ether for the elution of impurities, eluant 2: ethanol for the elution of II.1).

Yield: 0.83 g (40%), empirical formula: $C_{20}H_{26}N_2O$, color: whitish beige 1H-NMR ($CDCl_3$): 0.96 (6H, d, CH(C$\underline{H}_3)_2$, J=6.6 Hz), 1.09 (6H, d, CH—(C$\underline{H}_3)_2$, J=6.2 Hz), 3.18 (2H, sept, 2×C$\underline{H}$($CH_3)_2$), 3.47 (3H, s, N—$CH_3$), 6.95 (2H, pseudo-d, phenyl), 7.01–7.12 (3H, m, phenyl), 7.17–7.25 (3H, m, phenyl) 13C-NMR ($CDCl_3$): 21.9, 25.4 (CH($\underline{C}H_3)_2$), 28.2 ($\underline{C}H(CH_3)_2$), 43.7 (N—$CH_3$), 123.2, 127.3, 127.8, 128.2, 128.9, 130.1 (C-phenyl), 131.9 (quaternary C, phenyl), 146.2 (C=N—$\underline{C}$, quaternary C, phenyl), 149.1 (C=N) IR (KBr, $cm^{-1}$): 3056 (w), 2962 (m), 2869 (m), 1630 (vs), 1586 (m) 1505 (m), 1470 (s), 1445 (m), 1432 (m), 1383 (m), 1324 (m), 1225 (m), 1187 (s), 1162 (m), 1105 (s), 1077 (w), 1044 (m), 971 (m) 917 (w), 807 (s), 780 (s), 758 (s), 700 (s)

MS (FAB): $[M+H]^+$ (FAB)=311.2 m/z

1.2. Preparation of the Protonated Ligand II.2

Example 1.1 was Repeated Using the Acid Amide III.2

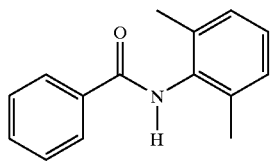

III.2

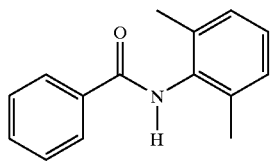

II.2

Yield: 1.63 g (63%), empirical formula: $C_{16}H_{18}N_2O$, color: white 1H-NMR ($CDCl_3$): 2.16 (6H, s, 2×$CH_3$), 3.47 (3H, s, N—$CH_3$), 6.82–6.92 (3H, m, phenyl), 7.08–7.27 (5H, m, phenyl) 13C-NMR ($CDCl_3$): 18.6 ($CH_3$), 43.6 (N—$CH_3$), 126.6, 127.7, 128.0, 128.2, 128.5 (C-phenyl), 130.1, 135.4, 135.5 (quaternary C, phenyl), 149.0 (C=N) IR (KBr, $cm^{-1}$): 1627 (vs), 1590 (m), 1578 (m), 1505 (m), 1472 (m), 1445 (m), 1426 (m), 1341 (m), 1258 (m), 1237 (s), 1179 (s), 1158 (m), 1106 (m), 1092 (m), 1079 (w), 1048 (m), 1025 (m), 957 (vs), 783 (vs), 774 (vs), 762 (vs), 754 (vs), 726 (s), 700 (vs)

MS (EI): $M^+$=254.2 m/z

1.3. Preparation of the Protonated Ligand II.3

Example 1.1 was Repeated Using the Amide III.2

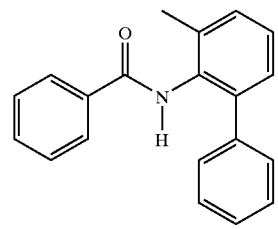

III.3

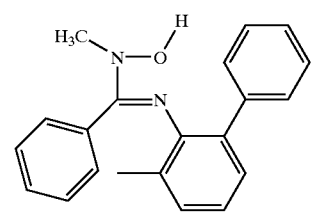

II.3

Yield: 1.39 g (48%), empirical formula: $C_{20}H_{18}N_2O$, color: whitish beige 1H-NMR ($CDCl_3$): 3.38 (3H, s, N—$CH_3$), 6.48–6.51 (1H, m, phenyl), 6.89–7.02 (4H, m, phenyl), 7.11–7.14 (1H, m, phenyl), 7.25–7.42 (8H, m, phenyl) 13C-NMR ($CDCl_3$): 43.5 (N—$CH_3$), 122.5, 124.0, 127.4, 127.5, 127.9, 128.7, 128.9, 129.0, 130.1, 130.7 (C-phenyl, C-biphenyl), 134.7, 135.5 (quaternary C, phenyl), 138.4 (C=N—$\underline{C}$, quaternary C, biphenyl), 146.8 (C=N) IR (KBr, $cm^{-1}$): 3257 (w), 2946 (w), 1607 (s), 1580

(m), 1509 (s), 1488 (s), 1447 (m), 1436 (s), 1422 (s), 1393 (m), 1387 (m), 1243 (s), 1196 (s), 1073 (m), 963 (s), 783 (m), 770 (vs), 756 (vs), 743 (vs), 698 (vs)

MS (EI): $M^+$=302.2 m/z

Example 1.4. Synthesis of the Protonated Ligand II.4

Example 1.1. was Repeated Using the Amide III.4

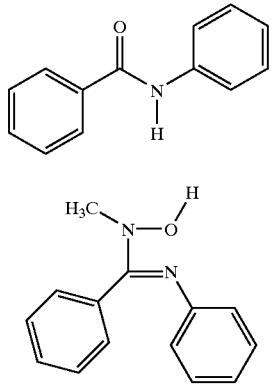

Yield: 1.03 g (42%), empirical formula: $C_{14}H_{14}N_2O$, color: whitish beige 1H-NMR ($CDCl_3$): 3.47 (3H, s, N—$CH_3$), 6.56 (2H, d, phenyl), 6.87 (1H, pseudo-t, phenyl), 7.01 (2H, pseudo-t, phenyl), 7.25 (2H, pseudo-d, phenyl), 7.24–7.43 (3H, m, phenyl) 13C-NMR ($CDCl_3$): 43.4 (N—$CH_3$), 121.0, 123.3, 127.8, 128.6, 129.0, 129.1, 130.4 (C-phenyl), 138.1 (C=N—$\underline{C}$, quaternary C, phenyl), 146.7 (C=N, quaternary C) IR (KBr, $cm^{-1}$): 3049 (w), 2943 (w), 1615 (vs), 1603 (s), 1574 (m), 1509 (s), 1482 (m), 1447 (m), 1428 (m), 1196 (s), 1160 (m), 1071 (w), 971 (s), 758 (s), 726 (s), 697 (vs)

MS (EI): $M^+$=226.1 m/z

Example 1.5

Example 1.1. was Repeated Using N-isopropylhydroxylamine Hydrochloride IV.5

Yield: 0.63 g (36%), empirical formula: $C_{22}H_{30}N_2O$, color: light yellow m.p.: 94–96° C.

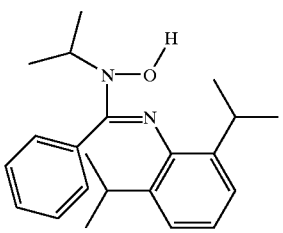

1H-NMR ($CDCl_3$): 0.98 (6H, d, Ph—CH—($C\underline{H}_3$)$_2$, J=6.2 Hz), 1.11 (6H, d, Ph—CH—($C\underline{H}_3$)$_2$, J=6.2 Hz), 1.37 (6H, d, N—CH—($C\underline{H}_3$)$_2$, J=6.6 Hz), 3.16 (2H, sept, 2×Ph—C$\underline{H}$—($CH_3$)$_2$), 4.03 (1H, sept, N—C$\underline{H}$—($CH_3$)$_2$, J=6.6 Hz), 6.95 (2H, pseudo-d, phenyl), 7.02–7.12 (3H, m, phenyl), 7.20–7.27 (3H, m, phenyl) 13C-NMR ($CDCl_3$): 20.0, 21.9, 25.4, 28.2 (CH($\underline{C}H_3$)$_2$, $\underline{C}H(CH_3)_2$), 54.8 (N—$CH_3$), 123.0, 127.5, 127.7, 128.3, 128.5, 129.9 (C-phenyl), 132.5 (quaternary C, phenyl), 145.9 (C=N—$\underline{C}$, quaternary C, phenyl), 148.1 (C=N) IR (KBr, $cm^{-1}$): 3433 (w), 3064 (w), 3006 (w), 2968 (s), 2948 (m), 2931 (m), 2867 (m), 1683 (w), 1598 (vs), 1503 (s), 1461 (s), 1436 (m), 1385 (m), 1378 (m), 1360 (s), 1343 (w), 1335 (w), 1320 (w), 1256 (w), 1173 (vs), 1123 (w), 1104 (w), 1067 (vs), 1040 (w), 978 (m), 930 (w), 924 (w), 822 (w), 808 (s), 781 (m), 760 (s), 702 (s)

MS (EI): $M^+$=338.3 m/z

Example 1.6

Preparation of the Protonated Ligand II.6

Example 1.1. was Repeated Using N-para-tolylhydroxylamine

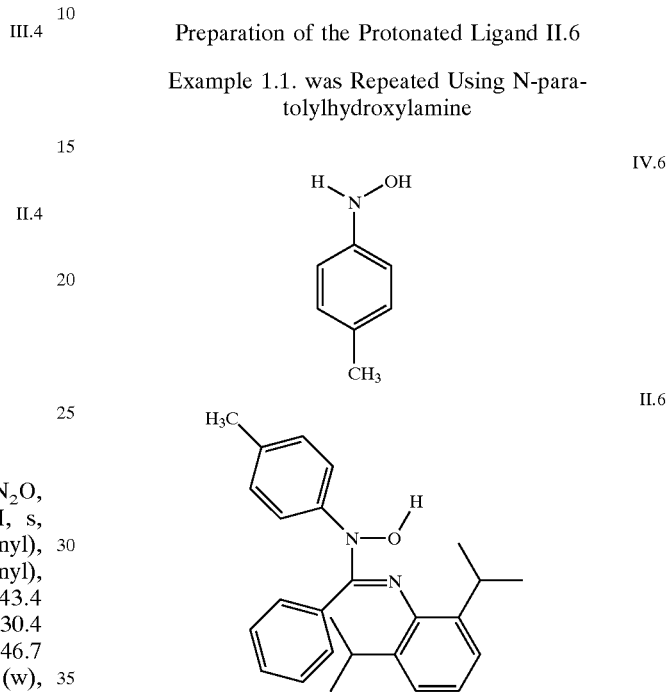

The preparation of IV.6 was carried out as follows:

0.7 g of p-$NO_2$-toluene (5.1 mmol) was placed in a 50 ml round-bottomed flask and partly dissolved in 6 ml of methanol. After addition of $NH_4Cl$ (0.27 g, 5.0 mmol) dissolved in 2 ml of water, the resulting suspension was heated under reflux as described in *Liebigs Ann. Chem.* 1985, 4, 673. Zinc powder was added in portions of 400 mg (2×) and 600 mg (2×) in the order indicated. After the 4th addition (total of 2 g, 31 mmol) and refluxing for 1 hour, thin layer chromatography indicated that there was no longer any starting material present.

The contents of the reaction flask were poured into a glass beaker filled with water. Excess zinc was filtered off, and the filtrate was transferred to a separating funnel and extracted 3× with 25 ml each time of methylene chloride. The combined organic phases were dried over $Na_2SO_4$. After taking off the solvent on a rotary evaporator, the resulting yellow solid was dried in a high vacuum.

Yield: 0.53 g (4.3 mmol)

The product was subsequently worked up by a method analogous to that in the preparation of II.1.

Yield: 0.30 g (18%), empirical formula: $C_{26}H_{30}N_2O$, color: brown 1H-NMR ($CDCl_3$): 0.90 (6H, d, CH($C\underline{H}_3$)$_2$, J=7.0 Hz), 1.11 (6H, d, CH($C\underline{H}_3$)$_2$, J=7.0 Hz), 2.19 (3H, s, N—Ph—$C\underline{H}_3$), 3.17 (2H, sept, 2×C$\underline{H}$($CH_3$)$_2$, J=7.0 Hz), 6.82–6.91 (4H, m, phenyl), 6.96–7.23 (8H, m, phenyl) 13C-NMR ($CDCl_3$): 14.0, 20.9, 22.0, 22.5, 25.2, 28.4, 31.5 (5×$CH_3$, 2×CH), 123.4, 125.4, 127.4, 127.8, 127.9, 129.0, 129.6, 129.7 (C-phenyl), 132.1, 137.4 (quaternary C, phenyl), 141.0 (N—C, quaternary C, phenyl), 145.4 (C=N—C, quaternary C, phenyl), 150.5 (C=N) IR (KBr, cm$^{-1}$): 2964 (s), 2927 (m), 2867 (m), 1600 (vs), 1571 (s) 1507 (s), 1461 (s), 1322 (m), 1302 (w), 1285 (w), 1260 (m), 1239 (m), 1187 (w), 1106 (m), 1077 (w), 1044 (m), 818 (s), 787 (s), 776 (s), 758 (s), 697 (s)

MS (FAB): [M$^+$H]$^+$=387.3 m/z

Example 1.7. Preparation of the Protonated Ligand II.7

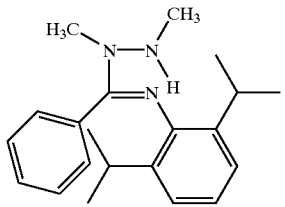

II.7

In the preparation of II.7, N,N'-dimethylhydrazine served as reagent and as base. No triethylamine was added. The procedure was modified as follows:

N,N'-Dimethylhydrazine (0.58 ml, 0.46 g, 7.7 mmol) was placed in a Schlenk tube which had been baked out and flushed with argon and was dissolved in absolute ethanol (50 ml).

Imide chloride III.1 (10 ml, 1.08 g, 3.6 mmol, c=0.115 g/ml) dissolved in methylene chloride was slowly added from a dropping funnel at −45° C. over a period of 60 minutes. After warming to room temperature, the reaction mixture was stirred for 1 hour (color change: colorless→yellow). The hydrazinium salt formed in the reaction precipitated, resulting in a turbid suspension. Thin layer chromatography (diethyl ether/hexane=1/1) subsequently indicated complete conversion.

The reaction mixture was poured into water (about 100 ml), and the product was extracted 3× with 50 ml each time of diethyl ether. The combined organic phases were dried over Na$_2$SO$_4$, and the desiccant was filtered off. After taking off the solvent on a rotary evaporator, the resulting viscous oil was dried in a high vacuum.

Yield: 1.10 g (94%), empirical formula: C$_{21}$H$_{29}$N$_2$O, color: brown 1H-NMR (CDCl$_3$): 0.94 (6H, d, CH(CH$_3$)$_2$, J=7.0 Hz), 1.06 (6H, d, CH(CH$_3$)$_2$, J=6.6 Hz), 2.64 (3H, s, CH$_3$—NH), 2.90 (3H, s, N—CH$_3$) 2.94 (2H, sept, 2× CH(CH$_3$)$_2$), 6.78–6.86 (3H, m, phenyl), 7.01–7.14 (5H, m, phenyl) 13C NMR (CDCl$_3$): 21.8, 24.1 (CH (CH$_3$)$_2$), 28.1 ( CH(CH$_3$)$_2$), 36.4 (NH—CH$_3$), 39.2 (N—CH$_3$), 122.1, 122.2, 127.8, 128.1, 128.8, 133.1, 138.2 (C-phenyl), 144.7 (C=N—C, quaternary C, phenyl), 157.3 (C=N) IR (KBr, cm$^{-1}$): 3244 (w), 3062 (w), 3022 (w), 2973 (m), 2960 (m), 1609 (vs), 1596 (s), 1586 (vs), 1576 (s), 1492 (w), 1439 (m), 1382 (m), 1364 (s), 1329 (m), 1262 (m), 1183 (w), 1111 (m), 1069 (s), 1046 (m), 1025 (s), 924 (m), 845 (s), 824 (m), 808 (w), 799 (m), 772 (vs), 760 (vs), 714 (vs), 700 (vs)

MS (EI): M$^+$=323.3 m/z

TABLE 1

Overview of protonated ligands of the formula II

| Prot. ligand | R$^1$ | R$^2$ | R$^3$ | Nu |
|---|---|---|---|---|
| II.1 | 2,6-(i-C$_3$H$_7$)$_2$C$_6$H$_3$ | C$_6$H$_5$ | CH$_3$ | O |
| II.2 | 2,6-(CH$_3$)$_2$C$_6$H$_3$ | C$_6$H$_5$ | CH$_3$ | O |
| II.3 | 2-(C$_6$H$_5$)—C$_6$H$_4$ | C$_6$H$_5$ | CH$_3$ | O |
| II.4 | C$_6$H$_5$ | C$_6$H$_5$ | CH$_3$ | O |
| II.5 | 2,6-(i-C$_3$H$_7$)$_2$C$_6$H$_3$ | p-CH$_3$—C$_6$H$_4$ | i-C$_3$H$_7$ | O |
| II.6 | 2,6-(i-C$_3$H$_7$)$_2$C$_6$H$_3$ | p-CH$_3$—C$_6$H$_4$ | CH$_3$ | O |
| II.7 | 2,6-(i-C$_3$H$_7$)$_2$C$_6$H$_3$ | C$_6$H$_5$ | CH$_3$ | N—CH$_3$ | i-C$_3$H$_7$: isopropyl; p-CH$_3$—C$_6$H$_4$: para-tolyl

2. Syntheses of the Complexes 2.1. Syntheses of Complexes of the Formula Ia

II.1 (0.28 g, 0.90 mmol) was placed in a baked out Schlenk tube which had been flushed with argon, and dissolved in 20 ml of THF (absolute), deprotonated at −80° C. in a cold bath (EtOH, N$_2$) by means of n-buthyllithium (0.45 ml, 0.90 mmol, 2.0 M in pentane) (color change: orange→dark red) and stirred at the temperature indicated for 1 hour.

After addition of the transition metal halide (ZrCl$_4$, 0.21 g, 0.90 mmol) at −80° C., the cold bath was removed and the solution was subsequently stirred overnight.

The THF was taken off in a high vacuum and the orange-brown residue was suspended in 50 ml of methylene chloride (absolute). The LiCl formed in the reaction was filtered off from the suspension. The solution was subsequently evaporated to dryness in a high vacuum, the residue was digested once with 10 ml of hexane (absolute) and washed. The solvent was syphoned off, and the pulverulent orange complex I.a.1 was dried in a high vacuum.

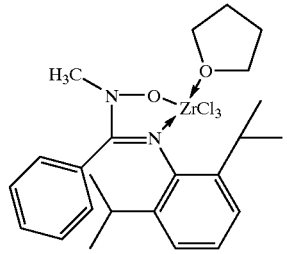

Ia.1

Yield: 0.41 g (90%), empirical formula: C$_{20}$H$_{25}$Cl$_3$N$_2$OZr, color: orange 1H-NMR (CD$_2$Cl$_2$): 1.04 (6H, d, CH(CH$_3$)$_2$), 1.32 (6H, d, CH(CH$_3$)$_2$), 1.81 (CH$_2$, broad, coordinated THF), 3.33 (5H, m, N—CH$_3$, 2×C H(CH$_3$)$_2$, signals superimposed), 3.83 (CH$_2$—O, broad, coordinated THF), 6.94–7.02 (3H, m, phenyl), 7.10–7.35 (5H, m, phenyl) 13C-NMR (CD$_2$Cl$_2$): 24.2, 25.9 (CH( CH$_3$)$_2$), 28.1 (CH(CH$_3$)$_2$), 41.6 (N—CH$_3$), 123.6, 124.2, 126.1, 128.5, 128.7, 129.1, 129.3, 129.4, 130.6, 143.9, 144.2 (C-phenyl), 161.7 (C=N).

In an analogous way, the complex Ia.2 was obtained by reaction of deprotonated II.2 with ZrCl$_4$.

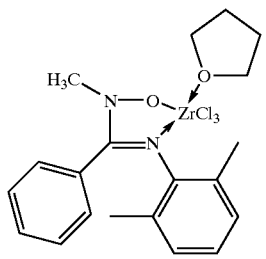

Ia.2

Yield: 0.82 g (86%), empirical formula: $C_{16}H_{17}Cl_3N_2OZr$, color: orange 1H-NMR ($CD_2Cl_2$): 1.91 ($CH_2$, broad, coordinated THF), 2.28, 2.31, 2.34, 2.39 (6H, 4×s, Ph—C$\underline{H}_3$, isomers), 3.27, 3.33 (3H, 2×s, N—C$\underline{H}_3$, isomers), 3.85 ($CH_2$—O, broad, coordinated THF), 4,53 ($CH_2$—O, broad, coordinated THF), 6.83–7.37 (8H, m, phenyl) 13C-NMR ($CD_2Cl_2$): 18.7, 19.5, 19.7, 20.7, 20.9 (Ph—$\underline{C}H_3$, isomers), 25.8 ($CH_2$, THF), 39.5, 41.3, 41.9, 42.2 (N—$\underline{C}H_3$, isomers), 69.3 ($CH_2$—O, THF), 125.5, 126.0, 127.2, 127.9, 128.0, 128.1, 128.4, 128.7, 128.9, 129.2, 130.1, 130.3, 130.4, 130.5, 130.9, 131.4, 133.1, 133.4, 133.8, 134.4, 134.7, 146.3 (phenyl, isomers), 161.3 (C=N).

In an analogous way, the complex Ia.3 was obtained by reaction of the protonated II.3 with $ZrCl_4$.

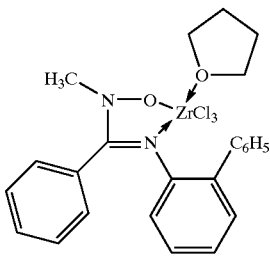

Ia.3

Yield: 0.71 g (88%), empirical formula: $C_{20}H_{17}Cl_3N_2OZr$, color: brown 1H-NMR ($CD_2Cl_2$): 1.88 (4H, 2×$CH_2$, broad, coordinated THF), 2.00 ($CH_2$, coordinated THF, shoulder), 2.33, 2.84, 2.97, 3.15 (3H, s, N—$CH_3$, plurality of singlets which add up to a total of 3 H, isomers, signal at 2.84 has the highest intensity), 3.82 (4H, 2×$CH_2$—O, broad, coordinated THF), 4.56 ($CH_2$—O, broad, coordinated THF), 6.90–7.43 (14H, m, phenyl) 13C-NMR ($CD_2Cl_2$): 25.9 ($CH_2$, THF), 41.1 (N—$CH_3$), 69.2 ($CH_2$—O, THF), 126.3, 127.2, 127.8, 127.9, 128.1, 128.5, 128.6, 128.7, 129.3, 129.4, 129.7, 130.2, 130.3 (C-phenyl), 131.2, 139.9 (quaternary C, phenyl), 144.5 (C=N—$\underline{C}$, quaternary C, phenyl),160.9 (C=N).

In an analogous way, the complex Ia.4 was obtained by reaction of deprotonated II.4 with $ZrCl_4$.

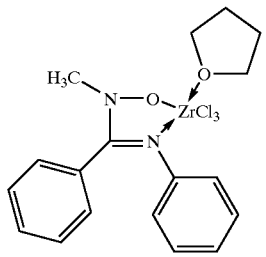

Ia.4

Yield: 0.58 g (92%), empirical formula: $C_{14}H_{13}Cl_3N_2OZr$, color: yellow 1H-NMR ($CD_2Cl_2$): 1.86 (4H, 2×$CH_2$, coordinated THF), 2.78, 3.32 (3H, 2×s, N—$CH_3$, isomers, signal at 2.78 has the highest intensity), 3.84 (4H, broad, 2×$CH_2$—O, coordinated THF), 4.54 ($CH_2$—O, coordinated THF), 6.92–7.35 (10H, m, phenyl) 13C-NMR ($CD_2Cl_2$): 25.8 ($CH_2$, THF), 40.0 (N—$CH_3$), 125.2, 126.5, 128.3. 128.4, 128.6, 128.8, 129.0, 129.1, 129.2, 130.8 (C-phenyl), 146.3 (C=N—$\underline{C}$, quaternary C, phenyl), 159.3 (C=N).

In an analogous way, the complex Ia.5 was obtained by reaction of deprotonated II.5 with $ZrCl_4$.

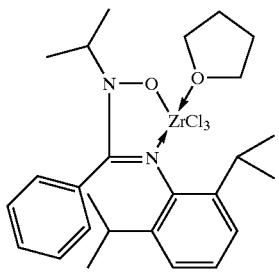

Ia.5

Yield: 0.28 g (64%), empirical formula: $C_{22}H_{29}Cl_3N_2OZr$, color: white 1H-NMR ($CD_2Cl_2$): 1.00–1.45 (15H, m, 2×Ph—CH(C$\underline{H}_3$)$_2$, N—CH(C$\underline{H}_3$), 1.61 (3H, d, N—CH(C$\underline{H}_3$), J=6.6 Hz), 1.83 ($CH_2$, broad, coordinated THF), 2.10 ($CH_2$, broad, coordinated THF), 3.28–4.02 (3H, m, 3×C$\underline{H}$($CH_3$)$_2$, superimposed septets), 3.76 ($CH_2$—O, broad, coordinated THF), 4.70 ($CH_2$—O, broad, coordinated THF), 6.92–7.15 (2H, m, phenyl), 7.18–7.46 (6H, m, phenyl) 13C-NMR ($CD_2Cl_2$): 20.0, 20.1, 22.0, 23.8, 24.3, 25.9, 26.1, 26.3, 28.2, 29.0, 29.2 (CH($\underline{C}H_3$)$_2$, $\underline{C}H(CH_3)_2$, isomers), 55.1 (N—CH), 123.5, 123.6, 123.8, 124.1, 126.1, 126.3, 127.9, 128.5, 128.6, 128.8, 129.0, 129.2, 129.6, 129.7, 130.5, 131.9, 143.8, 144.5, 146.9, 147.4, 155.0 (phenyl, isomers), 162.0 (C=N).

In an analogous way, the complex Ia.6 was obtained by reaction of deprotonated II.6 with $ZrCl_4$.

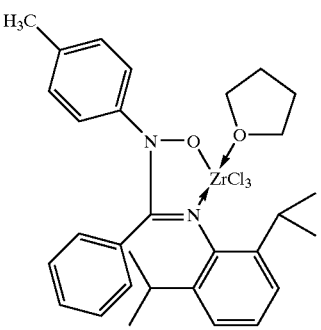

Ia.6

Yield: 0.29 g (90%), empirical formula: $C_{26}H_{29}Cl_3N_2OZr$, color: beige 1H-NMR ($CD_2Cl_2$): 1.05–1.35 (12H, m, 2×CH(C$\underline{H}_3$)$_2$), 1.82 ($CH_2$, broad, coordinated THF), 1.97 ($CH_2$, coordinated THF, shoulder), 2.27 (3H, s, N—Ph—C$\underline{H}_3$), 3.20, 3.40 (2H, 2×sept, C$\underline{H}(CH_3)_2$), 3.77 ($CH_2$—O, broad, not coordinated THF), 4.48 ($CH_2$—O, coordinated THF), 6.77–7.67 (12H, m, phenyl).

In an analogous way, the complex Ia.7 was obtained by reaction of deprotonated II.7 with $ZrCl_4$.

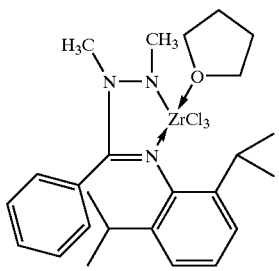

Ia.7

Yield: 0.,71 g (85%), empirical formula: $C_{21}H_{28}Cl_3N_3Zr$, color: yellow 1H-NMR ($CD_2Cl_2$): 0.93–1.24 (12H, 4×d, 2×CH(C$\underline{H}_3$)$_2$), 1.82 (CH$_2$, broad, coordinated THF), 2.94, 3.07, 3.18, 3.29 (5H, 4×s, sept, N—CH$_3$, 2×C$\underline{H}$(CH$_3$)$_2$, isomers, signal at 3.18 has the highest intensity), 3.39, 3.48, 3.57, 3.89 (3H, 3×s, N—CH$_3$, isomers), 3.84 (CH$_2$—O, coordinated THF), 4.56 (CH$_2$—O, coordinated THF), 6.90–7.60 (8H, m, phenyl) 13C-NMR ($CD_2Cl_2$): 21.8, 22.6, 24.2, 25.3, 25.9, 27.0, 28.2, 29.2 (CH($\underline{C}H_3$)$_2$, $\underline{C}H(CH_3)_2$, isomers), 34.9, 38.8, 40.4 (N—CH$_3$, isomers), 123.0, 124.0, 124.3, 128.3, 128.6, 128.9, 129.5, 129.7, 129.8, 133.0 (C-phenyl, 2 isomers), 143.8, 144.0 (C=N—$\underline{C}$, quaternary C, phenyl, 2 isomers), 146.1 (C=N).

In an analogous way, the complex Ia.8 was obtained by reaction of deprotonated II.2 with TiCl$_4$.

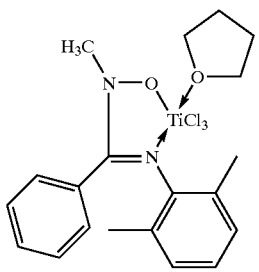

Ia.8

Yield: 0.67 g (95%), empirical formula: $C_{16}H_{17}Cl_3N_2OTi$, color: orange 1H-NMR ($CD_2Cl_2$): 2.13 (3H, s, Ph—C$\underline{H}_3$), 2.34 (3H, s, Ph—C$\underline{H}_3$), 3.40, 3.49, 3.63 (3H, s, N—CH$_3$, 3 singlets of decreasing intensity, total of 3H, isomers, signal at 3.40 ppm has the highest intensity), 6.85 (3H, pseudo-d, phenyl), 7.12–7.41 (5H, m, phenyl) 13C-NMR ($CD_2Cl_2$): 19.6, 20.4 (Ph—$\underline{C}H_3$), 30.0, 39.2, 41.5 (N—$\underline{C}H_3$, isomers), 125.8, 126.0, 128.1, 128.5, 128.7, 129.0, 129.3, 131.0 (C-phenyl), 131.7, 133.2, 133.5 (quaternary C, phenyl, isomers), 145.4, 149.9 (C=N—$\underline{C}$, quaternary C, phenyl, isomers), 160.3 (C=N)

In an analogous way, the complex Ia.9 was obtained by reaction of deprotonated II.2 with VCl$_4$.

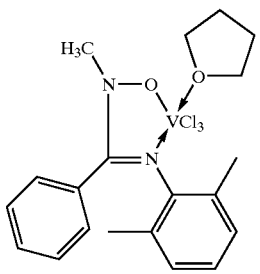

Ia.9

Yield: 0.58 g (91%), empirical formula: $C_{16}H_{17}Cl_3N_2OV$, color: dark green 1H-NMR: The complex is paramagnetic and no signals could be assigned.

In an analogous way, the complex Ia.10 was obtained by reaction of deprotonated II.7 with TiCl$_4$.

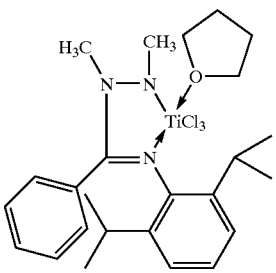

Ia.10

Yield: 0.56 g (95%), empirical formula: $C_{21}H_{28}Cl_3N_3Ti$, color: bluish green 1H-NMR ($CD_2Cl_2$): 1.05 (6H, d, CH(C$\underline{H}_3$)$_2$, J=6.9 Hz), 1.34 (6H, d, CH(C$\underline{H}_3$)$_2$, J=6.6 Hz), 2.93 (2H, sept, 2×C$\underline{H}$(CH$_3$)$_2$), 3.38 (3H, s, N—CH$_3$), 4.38 (3H, s, Ti—N—C$\underline{H}_3$), 6.99 (2H, pseudo-d, phenyl), 7.07–7.15 (3H, m, phenyl), 7.27–7.36 (3H, m, phenyl) 13C-NMR ($CD_2Cl_2$): 23.9, 25.3 (CH($\underline{C}H_3$)$_2$), 28.6 ($\underline{C}H(CH_3)_2$), 38.0 (N—$\underline{C}H_3$), 45.2 (Ti—N—$\underline{C}H_3$), 123.8, 128.0, 128.7, 128.9, 129.0, 131.4, 141.2 (C-phenyl), 150.9, (C=N—$\underline{C}$, quaternary C, phenyl), 160.0 (C=N).

TABLE 2

Overview of novel complexes of the formula I a

| Compound | R$^1$ | R$^2$ | R$^3$ | Nu | M |
|---|---|---|---|---|---|
| I a.1 | 2,6-(i-C$_3$H$_7$)$_2$C$_6$H$_3$ | C$_6$H$_5$ | CH$_3$ | O | Zr |
| I a.2 | 2,6-(CH$_3$)$_2$C$_6$H$_3$ | C$_6$H$_5$ | CH$_3$ | O | Zr |
| I a.3 | 2-(C$_6$H$_5$)—C$_6$H$_4$ | C$_6$H$_5$ | CH$_3$ | O | Zr |
| I a.4 | C$_6$H$_5$ | C$_6$H$_5$ | CH$_3$ | O | Zr |
| I a.5 | 2,6-(i-C$_3$H$_7$)$_2$C$_6$H$_3$ | p-CH$_3$—C$_6$H$_4$ | i-C$_3$H$_7$ | O | Zr |
| I a.6 | 2,6-(i-C$_3$H$_7$)$_2$C$_6$H$_3$ | p-CH$_3$—C$_6$H$_4$ | CH$_3$ | O | Zr |
| I a.7 | 2,6-(i-C$_3$H$_7$)$_2$C$_6$H$_3$ | C$_6$H$_5$ | CH$_3$ | N—CH$_3$ | Zr |
| I a.8 | 2,6-(CH$_3$)$_2$C$_6$H$_3$ | C$_6$H$_5$ | CH$_3$ | O | Ti |

TABLE 2-continued

Overview of novel complexes of the formula I a

| Compound | R¹ | R² | R³ | Nu | M |
|---|---|---|---|---|---|
| I a.9 | 2,6-(CH₃)₂C₆H₃ | C₆H₅ | CH₃ | O | V |
| I a.10 | 2,6-(i-C₃H₇)₂C₆H₃ | C₆H₅ | CH₃ | N—CH₃ | Ti | i-C₃H₇: isopropyl; p-CH₃—C₆H₄: para-tolyl

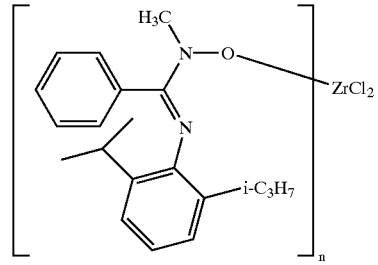

I b.1

2.2. Synthesis of Complexes of the Formula Ib

General procedure described by way of example for Ib.1

II.1 (0.65 g, 2.08 mmol) was placed in a baked-out Schlenk tube which had been flushed with argon and was dissolved in 20 ml of THF (absolute) to form a pink solution which was deprotonated at −110° C. in a cold bath (EtOH, N₂) by means of n-BuLi (1.2 ml, 2.4 mmol, 2.0 M in pentane) (color change: pink→yellow)

After addition of the transition metal halide (ZrCl₄, 0.21 g, 0.90 mmol, <1/2 meq) at −110° C., the mixture was stirred at this temperature for 1 hour. The cold bath was removed. After warming to room temperature, the mixture was stirred overnight, resulting in a clear, yellow solution.

The THF was taken off in a high vacuum and the residue was suspended in 50 ml of methylene chloride (absolute). The fine LiCl formed in the reaction was removed from the suspension by filtration (G4 frit and Celite®). The filtrate was subsequently evaporated to dryness in a high vacuum, and the residue was digested once with 10 ml of hexane (absolute) and washed. The solvent was syphoned off and the pulverulent yellow complex I.b.1 was dried in a high vacuum.

Yield: 0.54 g (77%), empirical formula: C₄₀H₅₀Cl₂N₄O₂Zr, color: whitish beige 1H-NMR (CD₂Cl₂): 0.23, 0.43, 0.92, 1.04 (24H, 4×d, 4×CH(C$\underline{H}$₃)₂), 4×J=6.6 Hz), 2.89 (2H, sept, 2×C$\underline{H}$(CH₃)₂), 3.18 (2H, sept, 2×C$\underline{H}$(CH₃)₂), 3.40, 3.54, 3.60, 3.97 (6H, 4×s, N—CH₃, isomers, signal at 3.60 has the highest intensity), 6.80–7.29 (16H, m, phenyl) 13C-NMR (CD₂Cl₂): 24.5, 25.1, 25.9, 26.2, 27.9, 28.1 (CH(C$\underline{H}$₃)₂, CH(C$\underline{H}$₃)₂), 43.6 (N—CH₃), 123.5, 124.2, 124.8, 125.8, 127.7, 127.9, 128.3, 128.7, 129.0, 129.4, 130.0, 130.3 (C-phenyl), 143.3, 143.5, 145.5 (C=N—$\underline{C}$, quaternary C, phenyl), 159.8 (C=N).

3. Polymerization Experiments

3.1. Polymerization in an Autoclave

The indicated amount of the complex to be studied, 2 ml of 30% strength by weight MAO solution in toluene (commercially available from Witco) and 400 ml of toluene were placed in a 1 l steel autoclave which had been made inert. The autoclave was pressurized with ethylene to a pressure of 40 bar at 70° C. This pressure was kept constant over the polymerization time of 90 minutes by introduction of further ethylene. The reaction was stopped by venting and the polymer was isolated by filtration, subsequent washing with methanol and drying under reduced pressure.

TABLE 3

Polymerization results

Ethylene polymerization (40 bar)

| Complex | Activity [gmmol⁻¹h⁻¹bar⁻¹] | Yield [g] | η [dl/g] | Time [min] | Amount of complex used [mg] |
|---|---|---|---|---|---|
| I a.1 | 50.2 | 9.5 | 9.51 | 30 | 4.8 |
| I a.2 | 45.1 | 12.0 | 14.01 | 30 | 6 |
| I a.3 | 68.4 | 4.8 | 11.41 | 35 | 1.5 |
| I a.4 | 78.7 | 6.7 | 24.95 | 60 | 0.9 |
| I a.5 | 88.4 | 11.9 | 4.43 | 90 | 1.2 |
| I a.6 | 51.3 | 8.8 | 8.76 | 75 | 2 |
| I a.7 | 76.8 | 6.2 | 15.6 | 45 | 1.4 |
| I a.8 | 18.8 | 7.4 | 54.33 | 60 | 4 |
| I a.9 | 5.3 | 6.2 | 19.18 | 90 | 8 |
| I a.10 | 28 | 1.0 | Not determined | 15 | 1.7 |
| I b.1 | 30.6 | 9.4 | 41.38 | 90 | 4 |

3.2 Copolymerization of Ethylene and Hexene

The procedure described under 3.1 was repeated, but 12.5 or 25 ml of 1-hexene were introduced into the autoclave at the beginning together with the other reagents.

TABLE 4

Copolymerization results

Copolymerization (ethene/hexene, 40 bar)

| Complex | Amount of 1-hexene added [ml] | Activity [gmmol⁻¹h⁻¹bar⁻¹] | Yield [g] | η [dl/g] | Time [min] | Amount Of compex used [mg] |
|---|---|---|---|---|---|---|
| I a.4 | 12.5 | 131.1 | 12.4 | 11.40 | 60 | 1.0 |
| I a.4 | 25 | 39.2 | 5.1 | 4.63 | 75 | 1.1 |
| I a.8 | 12.5 | 13.2 | 7.0 | 9.94 | 85 | 3.8 |
| I a.8 | 25 | 8.7 | 1.7 | 7.53 | 30 | 4.0 |

We claim:
1. A complex of the formula Ia or Ib,

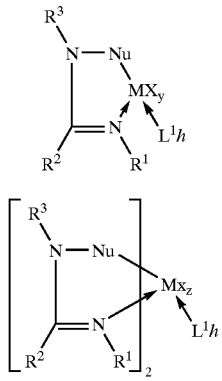

where the variables are defined as follows:
Nu is selected from the group consisting of O, S, N—$R^4$, P—$R^4$ and combinations thereof,
M is selected from the group consisting of Ti, Zr, Hf, V, Nb, Ta, Cr, Ni, Pd and combinations thereof,
h is an integer from 0 to 4;
y corresponds to the oxidation state of M minus 1;
z corresponds to the oxidation state of M minus 2;
X are identical or different and are selected from the group consisting of halogen, $C_1$–$C_6$-alkoxy, acetylacetonate, N($R^5R^6$), $C_1$–$C_8$-alkyl, $C_3$–$C_{12}$-cycloalkyl, $C_7$–$C_{13}$-aralkyl, $C_6$–$C_{14}$-aryl and combinations thereof,
$R^1$, $R^4$ are identical or different and are selected from the group consisting of hydrogen,
 $C_1$–$C_{18}$-alkyl, substituted or unsubstituted,
 $C_2$–$C_{18}$-alkenyl, substituted or unsubstituted, having from 1 to 4 isolated or conjugated double bonds,
 $C_3$–$C_{12}$-cycloalkyl, substituted or unsubstituted,
 $C_7$–$C_{13}$-aralkyl,
 $C_6$–$C_{14}$-aryl, unsubstituted or substituted by one or more identical or different substituents selected from the group consisting of
  $C_1$–$C_{18}$-alkyl, substituted or unsubstituted,
  $C_2$–$C_{18}$-alkenyl, substituted or unsubstituted,
  $C_3$–$C_{12}$-cycloalkyl,
  $C_7$–$C_{13}$-aralkyl,
  $C_6$–$C_{14}$-aryl,
  halogen,
  $C_1$–$C_6$-alkoxy, substituted or unsubstituted,
  $C_6$–$C_{14}$-aryloxy,
  $SiR^5R^6R^7$, O—$SiR^5R^6R^7$ and combinations thereof,
 five- to six-membered nitrogen-containing heteroaryl radicals, unsubstituted or substituted by one or more identical or different substituents selected from the group consisting of
  $C_1$–$C_{18}$-alkyl, substituted or unsubstituted,
  $C_2$–$C_{18}$-alkenyl, substituted or unsubstituted,
  $C_3$–$C_{12}$-cycloalkyl,
  $C_7$–$C_{13}$-aralkyl,
  $C_6$–$C_{14}$-aryl,
  halogen,
  $C_1$–$C_6$-alkoxy,
  $C_6$–$C_{14}$-aryloxy,
  $SiR^5R^6R^7$, O—$SiR^5R^6R^7$ and combinations thereof,
$R^2$ is $C_6$–$C_{14}$-aryl, unsubstituted or substituted by one or more identical or different substituents, or a five- to six-membered nitrogen-containing heteroaryl radical, unsubstituted or substituted by one or more identical or different substituents, where the substituents are as defined above,
$R^3$ is $C_1$–$C_{18}$-alkyl, $C_2$–$C_{18}$-alkenyl, substituted or unsubstituted, having from one to 4 isolated or conjugated double bonds, $C_3$–$C_{12}$-cycloalkyl, substituted or unsubstituted, $C_7$–$C_{13}$-aralkyl, $C_6$–$C_{14}$-aryl, unsubstituted or substituted by one or more identical or different substituents, or a five- to six-membered nitrogen-containing heteroaryl radical, unsubstituted or substituted by one or more identical or different substituents, where the substituents are as defined above,
where adjacent radicals $R^1$ to $R^4$ may be joined to one another to form a 5- to 12-membered ring which may in turn bear substituents selected from the group consisting of $C_1$–$C_8$-alkyl, substituted or unsubstituted, $C_2$–$C_8$-alkenyl, substituted or unsubstituted, having from one to 4 isolated or conjugated double bonds, $C_3$–$C_{12}$-cycloalkyl, substituted or unsubstituted, $C_7$–$C_{13}$-aralkyl, $C_6$–$C_{14}$-aryl, and combinations thereof,
$L^1$ is an uncharged organic or inorganic ligand,
$R^5$ and $R^7$ are identical or different and are selected from the group consisting of hydrogen, $C_1$–$C_8$-alkyl, $C_3$–$C_{12}$-cycloalkyl, $C_7$–$C_{13}$-aralkyl, $C_6$–$C_{14}$-aryl and combinations thereof.

2. A complex as claimed in claim 1, wherein Nu is oxygen, M is selected from among Ti and Zr, h is not equal to 0 and X is halogen.

3. A complex as claimed in claim 1, wherein M is selected from the group consisting of Ni, Pd and combinations thereof, h is not equal to 0 and
$L^1$ is selected from the group consisting of
phosphines $(R^8)_xPH_{3-x}$,
amines $(R^8)_xNH_{3-x}$,
ethers $(R^8)_2O$,
$H_2O$,
alcohols $(R^8)OH$,
pyridine,
pyridine derivatives of the formula $C_5H_{5-x}(R^8)_xN$,
CO,
$C_1$–$C_{12}$-alkyl nitriles,
$C_6$–$C_{14}$-aryl nitriles,
ethylenically unsaturated double bond systems and combinations thereof,
where x is an integer from 0 to 3, and
$R^8$ are identical or different and are selected from the group consisting of $C_1$–$C_{18}$-alkyl, $C_2$–$C_{18}$-alkenyl, substituted or unsubstituted, having from one to 4 isolated or conjugated double bonds, $C_3$–$C_{12}$-cycloalkyl, substituted or unsubstituted, $C_7$–$C_{13}$-aralkyl, $C_6$–$C_{14}$-aryl, unsubstituted or substituted by one or more identical or different substituents, and five- to six-membered nitrogen-containing heteroaryl radicals, unsubstituted or substituted by one or more identical or different substituents and combinations thereof.

4. A process for the polymerization or copolymerization of olefins or of styrene which comprises utilizing complexes of the formula Ia or Ib as claimed in any of claims 1 to 3.

5. A process for preparing polyolefin waxes which comprises utilizing complexes of the formula Ia or Ib as claimed in any of claims 1 to 3 and a regulator.

6. A process for preparing complexes as claimed in claim 1 or 2, which comprises firstly deprotonating a protonated ligand of the formula II

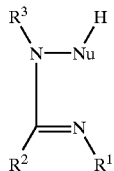

II by means of a base and subsequently reacting the product with a metal compound $MX_{y+1}$, where M is selected from the group consisting of Ti, Zr, Hf, V, Nb, Ta, Cr, Ni, Pd and combinations thereof and X is selected from the group consisting of halogen, $C_1$–$C_6$-alkoxy, acetylacetonate, $N(R^5R^6)$, $C_1$–$C_8$-alkyl, $C_3$–$C_{12}$-cycloalkyl, $C_7$–$C_{13}$-aralkyl, $C_6$–$C_{14}$-aryl and combinations thereof and $MX_{y+1}$ may optionally be stabilized by uncharged inorganic or organic ligands.

7. A process for preparing a supported catalyst for the polymerization or copolymerization of olefins, which comprises depositing one or more complexes as claimed in any of claims 1 to 3 and optionally an activator on a solid support.

8. A supported catalyst for the polymerization or copolymerization of olefins which comprises utilizing a process as claimed in claim 7.

9. A process for the polymerization or copolymerization of olefins which comprises utilizing a supported catalyst as claimed in claim 8.

10. A process for the emulsion polymerization or copolymerization of ethylene or other 1-olefins which comprises utilizing a complex of the formula Ia or b as claimed in claim 1 or 3.

11. A process as claimed in claim 5 wherein said regulator is hydrogen.

12. A process for the emulsion polymerization or copolymerization of ethylene or other 1-olefins and further olefins which comprises utilizing a complex of the formula Ia or b as claimed in claim 1 or 3.

* * * * *